United States Patent

Cosentino et al.

[11] Patent Number: 5,656,302
[45] Date of Patent: Aug. 12, 1997

[54] STABLE, SHIPPABLE, PEROXY-CONTAINING MICROBICIDE

[75] Inventors: Louis C. Cosentino, Plymouth; Anatol M. Hnojewyj, Minneapolis; Leroy J. Fischbach; Walter B. Jansen, both of Plymouth, all of Minn.; Jo-Ann B. Maltais, Lakewood, Colo.

[73] Assignee: Minntech Corporation, Minneapolis, Minn.

[21] Appl. No.: 487,325

[22] Filed: Jun. 7, 1995

Related U.S. Application Data

[60] Continuation of Ser. No. 228,492, Apr. 15, 1994, abandoned, which is a division of Ser. No. 32,395, Mar. 15, 1993, which is a continuation of Ser. No. 924,583, Aug. 6, 1992, abandoned, which is a continuation of Ser. No. 459,725, filed as PCT/US87/01147 May 14, 1987 published as WO88/08667 Nov. 17, 1988, abandoned.

[51] Int. Cl.$^6$ ............................................. A01N 39/00
[52] U.S. Cl. ................... 424/616; 424/613; 422/28; 422/29
[58] Field of Search .................... 424/613, 616; 422/28, 29

[56] References Cited

U.S. PATENT DOCUMENTS

| | | |
|---|---|---|
| 4,051,058 | 9/1977 | Bowing et al.. |
| 4,051,059 | 9/1977 | Bowing . |
| 4,297,298 | 10/1981 | Crommelynck . |
| 4,557,898 | 12/1985 | Greene et al. . |
| 4,587,264 | 5/1986 | Jourdan-Laforte . |
| 4,743,447 | 5/1988 | Le Rouzic et al. . |
| 4,812,173 | 3/1989 | Tsao et al. . |
| 4,963,157 | 10/1990 | Machida et al. . |
| 4,971,782 | 11/1990 | Rudy et al. . |
| 5,008,106 | 4/1991 | Merianos et al. . |
| 5,200,189 | 4/1993 | Oakes . |
| 5,508,046 | 4/1996 | Cosentino ............. 424/616 |

OTHER PUBLICATIONS

Shapilov et al., "Preparation and Properties of an Oxidizing System Based on Hydrogen Peroxide and Acetic Anhydride", Translated from Zhurnal Prikladnoi Khimii, vol. 44, No. 2, pp. 285–290, Feb. 1971.

Shapilov et al., "Preparation and Properties of an Oxidizing System Based on Acetic Acid and Hydrogen Peroxide", Translated from Zhurnal Prikladnoi Khimii, vol. 45, No. 9, pp. 2062–2066, Sep., 1972.

*Primary Examiner*—Brian M. Burn
*Attorney, Agent, or Firm*—Cushman Darby & Cushman Intellectual Property Group of Pillsbury Madison & Sutro, LLP

[57] ABSTRACT

A stable, shippable microbicidal composition including between about 0.2 to 8% hydrogen peroxide, about 0.2 to 11% peracetic plus acetic acid, 0 to about 1.0% sequestrant such as organic phosphonic acid or its salt and water, and surfactant between 0 and about 1% with the ratio of total acid to $H_2O_2$ being between about 1.0 and 11.

6 Claims, No Drawings

STABLE, SHIPPABLE, PEROXY-CONTAINING MICROBICIDE

This application is a continuation of 08/228,492, filed Apr. 15, 1994, now abandoned, which is a divisional of 08/032,395, filed Mar. 15, 1993, pending, which is a continuation of 07/924,583, filed Aug. 6, 1992, now abandoned, which is a continuation of 07/459,725, filed May 2, 1990, now abandoned which is a 371 of PCT/US/87/01147 filed May 14, 1987.

DESCRIPTION

1. Field of the Invention

The present invention relates to stable microbicides which contain levels of peroxy-containing compound and hydrogen peroxide which may be shipped in accordance with Title 49 Code of Federal Regulations (Department of Transportation Shipping Regulations) with few restrictions. More particularly, the present invention is directed to peracetic acid/hydrogen peroxide containing solutions which have a long storage stability and which retain effective microbicidal properties at room temperature, as well as at elevated temperatures. In the preferred from, invention formulations include a considerably greater quantity of peracetic acid plus acetic acid than the quantity of hydrogen peroxide. When referring to the combined quantity of peracetic acid plus acetic acid the term peracid will be used.

2. Background of the Invention

Peroxy-containing compositions have long been used as disinfectants due to their microbicidal activities. In the presence of multivalent metal cations peroxy compounds tend to decompose. To reduce this tendency, the use of stabilizers has been proposed. Another disadvantage of peroxy systems is that highly concentrated peroxy compounds which contain peracetic acid are very difficult to handle, are corrosive to the skin and are noxious. Highly concentrated forms may present a fire and explosion hazard. Venting of containers is mandatory. For these reasons, shipment of prior art formulations are only permissible in limited ways.

Prior investigators have proposed peroxy containing microbicides claimed to be stable in storage. Among these area patent to Bowing et al, U.S. Pat. No. 4,051,049. This patent discloses a formulation having from 0.5 to 20% peracetic acid or its precursor, 25–40% hydrogen peroxide and from zero to 5% of an anionic surfactant. Such formulations of disinfectants require venting of the storage container to prevent pressure build-up and rupture of the storage container. These prior formulations are unsuitable for shipment by some commercial carriers in accordance with current Code of Federal Regulations.

Because of the oxidizer nature of concentrated peroxy compounds, strict shipping regulations have been promulgated. Peroxy compounds in relatively high concentrations must be shipped in vented containers and cannot be shipped by air on commercial carriers due to the production of oxygen gas and subsequent venting of the gas from the shipping container.

Users of concentrates such as Bowing et al, supra, must be able to supply ultrapure water for dilution, and be equipped to handle the corrosive and noxious nature of such concentrates.

SUMMARY OF THE INVENTION

The invention provides a stable peroxy-containing microbicide which may be shipped by air in unvented containers. The microbicide contains less than 8% by weight and preferably less than 2% by weight of hydrogen peroxide and less than about 11% by weight and preferably less than 6% of total acid selected from the group consisting of peracetic acid, acetic acid, and mixtures thereof. Stability is achieved by formulating the microbicide such that the ratio of total acid to hydrogen peroxide is between about 1.0 and 11. Stability may be enhanced by sequestrants such as 1-hydroxyethylidene-1,1-diphosphonic acid and ethylenediaminetetracetic acid (EDTA) and the salts thereof capable of sequestering multivalent metal cations.

In addition, surfactants such as Sorbitan Monopalmitate Polyoxyethylene(2) Cetyl ether, Polyoxyethylene(20) Sorbitan Monopalmitate, Sodium Lauryl Sulfa, Triethanolamine Lauryl Sulfate may be included at concentration from 0 to about 1% to enhance the wetting and solubilizing action of the microbicide.

The microbicide so produced is an effective antimicrobial compound. When the formulation has approximately about 2% hydrogen peroxide, the microbicide may be shipped by air to wherever it is needed. The microbicide is quite stable due to the unique ratio of hydrogen peroxide to peracetic acid and acetic acid.

The advantages of the invention using peracetic acid as a constituent of the final product will be described. With the formulations of invention there will also exist quantities of acetic acid and of course hydrogen peroxide. Formulations in accordance with the invention containing approximately 2% hydrogen peroxide or less may be sealed into lightweight polyethylene bottles and stored and shipped with no significant pressure build-up over reasonable time periods. The solution may be used to disinfect human skin with no burning or bleaching effect. The product does not have a noxious odor, but rather a slight odor of acetic acid, like vinegar. It may be readily evaporated to leave essentially little or no residue.

DETAILED DESCRIPTION OF THE INVENTION

The stable, shippable microbicide is achieved by keeping the concentrations of hydrogen peroxide, acetic acid and peracetic acid low and importantly, by keeping the ratio of total acid.(meaning herein, peracetic acid, acetic acid and combinations thereof) to hydrogen peroxide between about 1.0 and about 11.

The microbicide may contain from about 0.2 to about 8% by weight hydrogen peroxide. Higher concentrations of hydrogen peroxide may be formulated but will not be as readily shippable. Oxygen evolution and pressure build up increases with increasing concentrations of hydrogen peroxide, When concentration of hydrogen peroxide is approximately 8% weight, after 3 to 4 days storage at room temperature, excessive pressure will occur in the container unless venting is provided to release the evolved gas. At concentrations of hydrogen peroxide greater than about 2%, oxygen pressure build-up on storage may require some venting for prolonged storage, however, the other desirable properties over the prior formulations remain. The total percent by weight of total acid expressed as acetic acid, peracetic acid and mixtures of peracetic acid and acetic acid, is between 0.2 and about 11% weight. The microbicide desirably may also include (but is not required to include) a sequestering compound as a stabilizer in the form of an organic phosphonic acid or its water-soluble acid salt capable of sequestering multivalent metal cations.

Ethylenediaminetetracetic acid (EDTA) or its sodium salt may also be used to sequester multivalent metal cations. The preferred stabilizer is an organic phosphonic acid such as 1-hydroxyethylidene-1, 1-diphosphonic acid. The sequestering agent may be added at a level of about 0 to about 1.0% by weight of the total mixture. The water used in formulating the compositions is preferably deionized.

In addition, surfactants may be included at concentrations from 0 to about 1% to enhance the wetting and solubilizing action of the microbicide.

Solutions described in the examples of this invention can be made in a number of ways including use of procedures generally set out in Bowing et al U.S. Pat. No. 4,051,059.

EXAMPLE I

A peroxy containing microbicide solution was prepared which contained 1% hydrogen peroxide, 0.08% peracetic acid, 5% acetic acid, 0.5% 1-hydroxyethylidene-1, 1-diphosphonic acid, and the balance deionized water. Concentration were certified by analysis.

Typical stability data at room for Example I is shown in Table 1.

TABLE 1

| | | | % Weight/Weight | | |
|---|---|---|---|---|---|
| No. of Days | pH 100% | Density at 22° C. | H2O2 | Peracetic Acid (PAA) | Acetic Acid (HOAc) |
| 1 | 1.88 | 1.0124 | 1.0498 | 0.0553 | 5.2472 |
| 4 | 1.93 | 1.012 | 1.0461 | 0.0610 | 5.2305 |
| 6 | 1.87 | | 1.0410 | 0.0760 | 5.2269 |
| 7 | 1.89 | 1.012 | 1.0394 | 0.0706 | 5.2206 |
| 11 | 1.92 | 1.0128 | 1.0332 | 0.0724 | 5.2079 |
| 14 | 1.89 | 1.0116 | 1.0210 | 0.0758 | 5.2209 |
| 18 | 1.88 | 1.012 | 1.0219 | 0.0730 | 5.1997 |
| 34 | 1.87 | | 1.0024 | 0.0761 | 5.2625 |
| 60 | 1.92 | | 1.0006 | 0.0835 | 5.2242 |
| 193 | 1.87 | | 0.9768 | 0.0900 | 5.2799 |

The microbicide of Example I is very stable exhibiting little change in hydrogen peroxide or acetic acid concentrations over time. The peracetic acid value increased over the half-year time period. This increase in peracetic acid concentration enhances the microbicidal activity of the microbicide solution and is hence desirable. Oxygen evolution during storage in sealed containers over this time period was negligible.

Microbicidal Effectiveness

The effectiveness of the microbicide of Example I was evaluated using the following methods certified by The Association of Official Analytical Chemists (A.O.A.C.) 14th edition (1984): (1) Use-Dilution Methods (Section 4.007–4.011). (2) Sporicidal Activity of Disinfectants Test (Section 4.033–4.035), and (3) Tuberculocidal Activity of Disinfectants Test(Section 4.036, 4.039–4.041). The A.O.A.C. Procedures are incorporated herein by reference.

Use Dilution Test

The organisms employed were Pseudomonas aeruginosa, ATCC 15442, Staphylococcus aureus, ATCC 6538 and Salmonella choleraesuis, ATCC 10708. Three lots of microbicide diluted 1:50 with sterile deionized water were tested against stainless steel carriers contaminated with a culture containing between about 6.7 and 9.0×108/ml of one of the above bacteria. In total, testing included exposure of 180 contaminated carriers to each lot of the diluted microbicide of the invention for 10 minutes. The microbicide was then neutralized by making primary and secondary subcultures of each carrier in fluid thioglycollate. After 48 hours incubation at 37° C. of subcultures, no growth of P. aeruginosa, S. aureus or S. choleraesuis was seen. No growth in 59 out of 60 carriers exposed to each lot of microbicide solution is necessary for a disinfection confidence level of 95%. Phenol resistance testing of the bacteria used showed growth i.e., resistance to a 1:90 and 1:100 dilution of phenol after exposure of 5, 10 and 15 minutes (P. aeruginosa); resistance to 1:70 dilution of phenol after exposure of 5, 10 and 15 minutes (S. aureus); resistance to 1:100 dilution of phenol after 5 and 10 but not 15 minutes of exposure (S. choleraesuis).

Sporicidal Test

Three lots of microbicide solution were utilized in a sporicidal test against porcelain penicylinders and silk suture loops contaminated with either Bacillus subtilis ATCC 19659 or Clostridium sporogenes ATCC 3584. In total 720 carriers equally distributed between the two organisms and two carrier types were tested vs. the formulation of the invention undiluted. All carriers passed, i.e. no organisms/ spores survived. No survivals can be tolerated for qualification of the solution by the Environmental Protection Agency as a sterilant. The spores were tested for two exposure periods, 5½ hours at 20° C. and 11 hours at 20×C. At the end of the exposure time, each carrier was neutralized in fluid thioglycollate by primary and secondary subculture. Subcultures were incubated for 21 days at 36° C. The tubes were heat shocked for 20 minutes at 80° C. after the 21 day incubation to activate any remaining spores. The tubes were then incubated for 72 hours at 36° C. The solution of Example I was completely-effective and no growth of either B. subtilis or C. sporogenes was found after the 5½ or 11 hours exposure of the organisms on porcelain penicylinders or silk suture loops. Acid resistance of the organisms was tested. B. subtilis was resistant to a five but not ten minute exposure of a loop and penicylinder to 2.5N Hydrochloric acid. C. sporogenes was resistant to a 2 but not 5 minute exposure of a loop and penicylinder to the acid. Minimum resistance requirement for each organism is 2 minutes.

Tuberculocidal Test

Two lots of microbicidal solution undiluted were utilized in an "in vitro" test to determine tuberculocidal activity. The tests were run at 20° C., contact exposure was 10 minutes. The incubation period was 90 days at 36° C. No positive carriers were found in the Middlebrook 7H9 Difco B, Kirchner or Proskauer-Beck (Modified) Media. The Mycobacterium bovis was resistant (showed growth) after a 10 minute exposure time to a 1:75 dilution of phenol solution when recovered on the Middlebrook 7H9 Difco B, Kirchner and Proskauer-Beck (Modified) Media.

The results of the AOAC procedure reference tests show that the microbicide of the invention, besides being stable and readily transportable is an effective antimicrobal agent.

EXAMPLE II

A peroxy/containing microbicidal solution was prepared which contained 6% hydrogen peroxide, 0.74% peracetic acid, 10% acetic acid, 1% 1-hydroxyethylidene-1, 1-disphosphonic acid, and the balance preferably deionized water. Concentrations were verified by analysis.

Typical stability data at room temperature for Example II is shown in Table 2.

TABLE 2

| No. of Days | pH 100% | Density at 22° C. | % Weight/Weight | | |
|---|---|---|---|---|---|
| | | | H2O2 | Peracetic Acid (PAA) | Acetic Acid (HOAc) |
| 11 | 1.80 | | 5.9067 | 0.6739 | 9.6192 |
| 16 | 1.37 | 1.048 | 5.9081 | 0.7058 | 9.5654 |
| 30 | 1.35 | | 5.8768 | 0.7401 | 9.5561 |
| 277 | 1.65 | | 5.11 | 0.698 | 9.84 |

As shown in Table 2 above, the 6% hydrogen peroxide containing microbicidal product is very stable and shows relatively little change in hydrogen peroxide or acetic acid concentrations over the test duration. There is a larger amount of oxygen evolution than with the solution of Example I or a solution containing 2% hydrogen peroxide. Venting of storage containers is desirable for the solution of Example II.

Microbicidal Effectiveness
Use Dilution Test

The effectiveness of the microbicide of Example II was evaluated using the Use-Dilution Test method of Example I except that the three lots of microbicide of Example II were diluted 1:35 with sterile deionized water. In addition, the stainless steel carriers-were contaminated with a culture containing between 2×108 and 1×109/ml of bacteria. The results of the Use-Dilution Test for the microbicidal solution of Example II were the same as the results for the microbicidal solution of Example I. No growth occurred.

Sporicidal Test

The effectiveness of the microbicide of Example II was evaluated using the Sporicidal Test described for Example I with the following modifications.

Three lots of the peroxy containing microbicidal solution of Example II were tested at a 20× dilution in sterile deionized water. No organisms/spores survived. Therefore, the microbicidal solution of Example II meets the requirements of the Environmental Protection Agency for labeling as a sterilant.

EXAMPLE III

A peroxy containing microbicidal solution was prepared containing 7.45% hydrogen peroxide, 0.1218% peracetic acid, 10.98% acetic acid, 0.5% 1-hydroxyethylidene-1, 1-disphosphonic acid, and 0.01% Sorbitan Monopalmitate, and the balance preferably deionized water. Concentrations were verified by analysis.

The solution of Example III was found to have microbicidal activity.

EXAMPLE IV

A peroxy containing microbicidal solution was prepared containing 7.3249% hydrogen peroxide, 0.1747% peracetic acid, 9.72% acetic acid, and the balance preferably deionized water. Concentrations were verified by analysis.

The solution of Example IV was found to have microbicidal activity.

EXAMPLE V

A peroxy containing microbicidal solution was prepared containing 7.3957% hydrogen peroxide, 0.2131% peracetic acid, 9.49% acetic acid, 0.01% Sorbitan Monopalmitate, and the balance preferably deionized water. The solution of Example V was found to have microbicidal activity.

As previously noted, it has been found that solutions containing 2% hydrogen peroxide, in accordance with the invention, exhibit marked resistance to the evolution of oxygen pressure in sealed containers. The advantages of this increased quantity of hydrogen peroxide over either the 1% or 8% solution is that a greater quantity of peracetic acid is available to the user while the undesirable build-up of oxygen gas pressure of the 8% solution is avoided by the 2% composition.

Other tests were performed and demonstrate the activity of the vapors of the present formulations of the invention as a microbicide. It has been found experimentally that even in the case of peroxy containing microbicide of Example I, the vapor is effective in sterilizing contaminated surfaces on exposure.

It has also been found that formulations in accordance with the invention can be reused, as evidenced when tested according to the Environmental Protection Agency Re-Use Test Protocol Specifications. This reuse capability is available even after repeated sterilizing has been performed with a given batch of material. Over a thirty day reuse study, formulations in accordance with Example I of the invention were subjected to a regimen of stressing with detergent pre-cleaned equipment soaking, resoaking and bioburden additions. At stipulated time periods, the solutions were analyzed for hydrogen peroxide, peracetic acid and acetic acid. The reused material continued to provide sterilization and disinfection after. 7, 14 and 30 day periods of reuse with no appreciable change in concentration of the ingredients.

Actual testing of microbicidal formulations within the limitations that hydrogen peroxide is from 0.2% to 8% by weight, acid, i.e., the total of peracetic acid and acetic acid, is from 1.0 to 11% by weight and where the ratio of acid to hydrogen peroxide is from 1.0 to 11 showed effective anti-microbial activity.

In considering the invention, it must be remembered that the examples described in the disclosure are illustrative only and that numerous variations within the teachings of the invention may be prepared possessing varying degrees of microbicidal activity, stability and oxygen gas pressure generation without departing from the spirit of the invention.

What is claimed is:

1. A microbicidal solution suitable for a non-vented container, the microbicidal solution comprising:
   a) from about 0.2 to about 8% by weight hydrogen peroxide;
   b) from about 0.2 to about 11% by weight of an acid mixture consisting of peracetic acid and acetic acid;
   c) from about 0.5 to about 1.0% by weight of a sequestering agent; and
   d) the remainder of said solution being water; and wherein, the ratio of said acid mixture to hydrogen peroxide is between about 1.0 to about 11; wherein the hydrogen peroxide concentration of said solution is approximately 3% by weight or less.

2. A method for sterilizing, disinfecting, or sanitizing a surface, said method comprising:
   contacting said surface with a dilute solution for use as a microbicide, the concentrate solution comprising:
   a) from about 0.2 to about 8% by weight hydrogen peroxide;
   b) from about 0.2 to about 11% by weight of an acid mixture consisting of peracetic acid and acetic acid;
   c) from about 0.5 to about 1.0% by weight of a sequestering agent; and
   d) the remainder of said concentrate solution being water; wherein, the ratio of said acid mixture to hydrogen peroxide is between about 1.0 to about 11 in said concentrate solution.

3. A method according to claim 2, wherein the step of contacting comprises contacting a stainless steel surface with said solution.

4. A method according to claim 2, wherein the step of contacting comprises the step of contacting an equipment surface with said solution.

5. A method according to claim 2, wherein the step of contacting comprises the step of contacting a porcelain surface with said solution.

6. A method according to claim 2, wherein the step of contacting comprises the step of contacting a surface of a silk suture loop with said solution.

* * * * *